United States Patent
Bova et al.

(10) Patent No.: US 11,318,123 B2
(45) Date of Patent: May 3, 2022

(54) METHODS AND COMPOSITIONS FOR TREATING GASTRIC ULCERS

(71) Applicant: LUODA PHARMA LIMITED, Dublin (IE)

(72) Inventors: Nicholas Bova, Caringbah (AU);
Sanjay Garg, Myrtle Bank (AU);
Stephen Page, Newtown (AU)

(73) Assignee: LUODA PHARMA LIMITED, Dublin (IE)

( * ) Notice: Subject to any disclaimer, the term of this patent is extended or adjusted under 35 U.S.C. 154(b) by 0 days.

(21) Appl. No.: 15/564,088

(22) PCT Filed: Dec. 8, 2016

(86) PCT No.: PCT/AU2016/051205
§ 371 (c)(1),
(2) Date: Oct. 3, 2017

(87) PCT Pub. No.: WO2017/096426
PCT Pub. Date: Jun. 15, 2017

(65) Prior Publication Data
US 2018/0133201 A1 May 17, 2018

(30) Foreign Application Priority Data

Dec. 8, 2015 (AU) .............................. 2015905078

(51) Int. Cl.
| A61K 31/4439 | (2006.01) |
| A61K 47/44 | (2017.01) |
| A61K 9/00 | (2006.01) |
| A61K 47/18 | (2017.01) |
| A61K 9/10 | (2006.01) |
| A61K 47/14 | (2017.01) |
| A61P 1/04 | (2006.01) |
| A61K 47/32 | (2006.01) |

(52) U.S. Cl.
CPC ........ *A61K 31/4439* (2013.01); *A61K 9/0019* (2013.01); *A61K 9/10* (2013.01); *A61K 47/14* (2013.01); *A61K 47/18* (2013.01); *A61K 47/183* (2013.01); *A61K 47/44* (2013.01); *A61P 1/04* (2018.01); *A61K 47/32* (2013.01)

(58) Field of Classification Search
CPC .... A61K 31/4439; A61K 9/0019; A61K 9/10; A61K 47/14; A61K 47/18; A61K 47/183; A61K 47/44; A61P 1/04
See application file for complete search history.

(56) References Cited

U.S. PATENT DOCUMENTS

2014/0163074 A1   6/2014  Stephan et al.

FOREIGN PATENT DOCUMENTS

| CN | 103239448 A | 8/2013 | |
| CN | 103637986 | * 3/2014 | |
| CN | 103637986 A | 3/2014 | |
| CN | 103222962 B | 12/2014 | |
| EP | 2601938 A1 | 6/2013 | |
| IN | 208337 B | 7/2005 | |
| WO | WO-2000/050038 A1 | 8/2000 | |
| WO | WO-2004/103291 A2 | 12/2004 | |
| WO | WO-2005/079752 A2 | 9/2005 | |
| WO | WO-2006070117 A1 | * 7/2006 | .......... A61K 9/1617 |
| WO | WO-2009/105118 A1 | 8/2009 | |

OTHER PUBLICATIONS

Translation of CN 103637986 via Escapenet.*
Hirano et al. (J. Phys, Chem. B (2010), vol. 114, pp. 13455-13462). (Year: 2010).*
Arginine PubChem 6322 [online] Retrieved from the internet, Retrieved on Apr. 22, 2019, <url:https://pubchem.ncbi.nlm.nih.gov/compound/L-arginine> (Year: 2004).*
Andrews et al. J. Vet. Intern Med., vol. 20,(2006) pp. 1201-1206 (Year: 2006).*
WO2006070117A1 translation from Espacenet (Year: 2006).*
Horse Report (Oct. 2012) Diagnosis and Treating Gastric Ulcers in Horses by Jorge Prieto p. 4-9 (Year: 2012).*
Kawasaki et al., Preparation and evaluation of a suppository dosage form containing omeprazole. *Pharmaceut. Sci.* 3: 431-4 (1997).
Tellez et al., Pharmacodynamic study of a long-acting parenteral formulation of omeprazole in horses. *J. Vet. Pharmacol. Therap.* 28: 587-9 (2005).
Videla et al., Effects of intravenously adminstered esomeprazole sodium on gastric juice pH in adult female horses. *J. Vet. Intern. Med.* 25: 558-62 (2011).

* cited by examiner

*Primary Examiner* — Taina D Matos Negron
(74) *Attorney, Agent, or Firm* — Marshall, Gerstein & Borun LLP (57) ABSTRACT

A method of treating and/or preventing gastric ulcers, said method comprising administering by injection a therapeutically effective amount of a composition comprising: c) a first agent selected from the group consisting of: a medium chain triglyceride and a long chain triglyceride; and d) a second agent comprising a proton pump inhibitor or pharmaceutically or veterinary acceptable salt, wherein the composition is adapted for sustained release of a therapeutically effective amount of the proton pump inhibitor to a subject in need thereof.

18 Claims, 5 Drawing Sheets

METHODS AND COMPOSITIONS FOR TREATING GASTRIC ULCERS

CROSS-REFERENCE OF RELATED APPLICATIONS

This application is the U.S. national phase of International Application No. PCT/AU2016/051205, filed 8 Dec. 2016, incorporated herein by reference in its entirety, which claims priority benefit of AU Patent Application No. 2015905078, filed 8 Dec. 2015.

TECHNICAL FIELD

This invention relates to methods and compositions for the treatment and prevention of gastric ulcers in a subject.

BACKGROUND ART

Equine Gastric Ulcer Syndrome (EGUS) describes the erosive and ulcerative diseases of the equine stomach which include both Equine Squamous Gastric Disease (ESGD) and Equine Glandular Gastric Disease (EGGD), terms that refer to the anatomical region of the stomach affected, which, in the case of EGGD, includes the cardia, fundus, antrum and pylorus.

EGUS prevalence has been shown to vary with breed, type of use, level of training, with different prevalence of ESGD and EGGD. Horses involved in training and racing are highly prone to developing EGUS, with greater than 80% of competing racehorses and high level endurance horses suffering from ESGD. Even in horses that rarely compete and are used mainly in their home environment, the prevalence of ESGD is around 11%. Ulcerative disease of the glandular stomach (EGGD) is not as well studied, but frequencies between 17 and 33% have been reported in endurance horses, 56-64% in leisure horses, and 47-65% in thoroughbred racehorses.

A variety of management factors contribute to the development of ESGD. All of these factors share the common trait that they increase the exposure of the squamous mucosa of the stomach to acid. In vitro experiments clearly show that squamous mucosal cells are susceptible to hydrochloric acid (HCl) and volatile fatty acid (VFA) injury in a pH, dose and time dependent manner. Damage of the outer cell barrier is induced by HCl. Damaged cells allow diffusion of acid into the squamous cells of the stratum spinosum ultimately resulting in ulceration.

The risk of EGUS is closely related to diet, especially the consumption of feeds rich in starch (for example, grain). Starches and sugars are fermented by gut bacteria to produce a variety of acids (including volatile fatty acids and lactic acid) that act together with HCL to produce ulceration.

Current therapeutic strategies follow the mantra "no acid, no ulcer" and focus on neutralising existing gastric acid or blocking new gastric acid secretion to increase stomach pH. Suppression of gastric acid production can be achieved by using proton pump inhibitors such as rabeprazole, lansoprazole, dexlansoprazole, tenatoprazole, omeprazole and esomeprazole.

The treatment of EGUS requires commitment to long term daily treatment and is difficult, particularly when horses are involved in performance, racing, eventing and other work. EGUS can be treated by protecting the damaged gastric mucosa with mucosal protectants such as sucralfate (which is given orally) and misoprostol (which is given by injection), by neutralising gastric acid with antacids such as magnesium hydroxide, or by suppressing acid production by the oral use of proton pump inhibitors (PPI) or histamine type 2 ($H_2$) receptor antagonists such as ranitidine.

Each of the current treatments has significant shortcomings. Mucosal protectants must be continuously present and available at all sites of ulceration to allow ulcers to heal. This requires high doses of the mucosal protectant and frequent administration, at last four times daily for both sucralfate and misoprostol. Similarly, antacids must be present constantly in the stomach and in sufficient quantity to neutralise the significant quantity of continuously produced gastric HCl. The most effective approaches are those which suppress acid production. The $H_2$ receptor antagonists act to block one stimulus of acid production in parietal cells via competitive inhibition of $H_2$ receptors. Acid suppression requires the $H_2$ receptor antagonist to be constantly circulating at a concentration sufficient to block the $H_2$ receptors and recommended dosage regimens include oral treatment every 8 hours. However, other stimulatory pathways for acid production by parietal cells are not inhibited by $H_2$ blockers. Consequently $H_2$ receptor antagonists do not provide reliable acid suppression. The proton pump inhibitors such as omeprazole irreversibly inhibit the H+, K+ ATPase pump in gastric parietal cells leading to prolonged acid suppression irrespective of the stimulus for acid production. However, currently available PPIs must be given orally at least once daily and their bioavailability is dependent on the diet of the recipient horse. Furthermore, they require approximately five days of daily oral administration to reach their maximum degree of acid suppression which is generally less than total acid suppression.

The duration of acid suppression within each day that is necessary to enable healing of EGUS has not been definitively determined. However, based on experience of ulcer healing in humans, it is generally considered that healing of equine gastric ulcers requires the presence of a gastric pH of at least 4 for a minimum of 16 hours each day. Published clinical studies have shown that oral omeprazole preparations may only provide 12 hours of adequate gastric acid suppression in horses (Merritt et al), suggesting that twice daily oral administration may be necessary in at least some cases.

The duration of treatment of EGUS has been the subject of considerable investigation and it has been concluded that 21-28 days of PPI administration is necessary for 70-80% of ESGD lesions to heal, while only 25% of EGGD lesions heal in 28-35 days. By analogy to the treatment of nonsteroidal anti-inflammatory drug induced ulcers (which share many features with EGGD) in humans, extended treatment of EGGD for 8-12 weeks may be necessary to achieve healing rates of 80% or above.

Omeprazole (a racemic compound which includes the R-isomer as well as the S-isomer that is also known as esomeprazole) is considered the most effective drug for inhibition of the gastric acid secretion in humans and in horses. It is a proton pump inhibitor and as a weak base is concentrated and becomes active only in the highly acid environment of the parietal cell secretory canaliculi where it is converted to the active sulfenamide moiety. The activated species binds irreversibly to cysteine residues to inhibit the specific gastric enzyme H+, K+–ATPase proton pump present in the parietal cell of the gastric mucosa. A single oral dose of omeprazole cannot inhibit all gastric acid pumps that are functioning in any one day, as the pharmacokinetic half-life of oral omeprazole is less than 3 hours (Sykes et al 2014) and gastric acid pumps are being recruited in parietal cells throughout the day (Shin and Sachs 2008). Uninhibited gastric acid pumps continue to actively transport hydrogen ions into the stomach, increasing acidity for much of the day and compromising the healing of gastric ulcers.

Omeprazole is used for the treatment of dyspepsia, peptic ulcer disease, gastroesophageal reflux disease (GORD), laryngopharyngeal reflux, erosive esophagitis, and Zollinger-Ellison syndrome in humans. For human use, omeprazole is available as tablets and capsules (containing omeprazole or omeprazole magnesium) in strengths of 10, 20, 40, and in some markets 80 mg; and as a powder (omeprazole sodium) for reconstitution in 0.9% sodium chloride or 5% glucose and intravenous infusion over a period of 20-30 minutes. Omeprazole is administered daily and is usually administered for 4 to 8 weeks for gastric ulcers or up to 12 months to manage erosive esophagitis. Esomeprazole is available for human use as esomeprazole magnesium in 20 and 40 mg capsules and as esomeprazole sodium powder (40 mg) for reconstitution and intravenous administration.

The requirement of at least a single daily dose of omeprazole and its unpredictable duration of acid suppression limits the clinical value of omeprazole. For example, GastroGard (NADA 141-123) and UlcerGard (NADA 1410227) are the only US FDA-approved once a day ulcer medication to treat equine stomach ulcers and LOSEC® (omeprazole), FDA-approved for humans, can maintain the pH≥4 but only up to 12-20 hours after a single administration and repeated daily doses are therefore required for optimal effectiveness.

Furthermore, omeprazole is a highly unstable drug substance because it is sensitive to light, humidity, temperature, pH, and organic as well as aqueous vehicles, leading to significant pharmaceutical challenges to formulate a stable product, accounting for the short shelf life of reconstituted omeprazole and esomeprazole injections.

Sandin et al (1999) noted that the available oral formulations of omeprazole were difficult to administer to horses and relatively expensive. They attempted to overcome these limitations by investigating the intramuscular administration of omeprazole monohydrate dissolved in saline. It was found that a single intramuscular injection of omeprazole at 1 mg/kg bodyweight resulted in 12 hours of pentagastrin-stimulated acid suppression or around 23 hours of reduced basal acid secretion, thus delivery still needed to be done at least once a day.

The subcutaneous administration of a long-acting formulation of omeprazole has also been proposed as a means of managing equine gastric ulcer syndrome. Tellez et al (2005) tried to overcome the need for daily or multiple daily oral treatment using a formulation of omeprazole suspended in a matrix of a copolymer of polyoxypropyl-polyoxyethylene. The preparation had to be administered to horses within two days of preparation as they found it was stable for only one week. Following subcutaneous administration, the authors concluded that gastric pH was increased. However, the injection caused significant site reactions and increased risk of clostridial infection.

The object of the invention is to overcome some or all of the short comings of the prior art, or at least provide an alternative treatment option.

The discussion of the background art set out above is intended to facilitate an understanding of the present invention only. The discussion is not an acknowledgement or admission that any of the material referred to is or was part of the common general knowledge as at the priority date of the application.

DISCUSSION OF THE INVENTION

In a first aspect of the invention, there is provided a method of treating and/or preventing gastric ulcers, said method comprising administering by injection a therapeutically effective amount of a composition comprising:
  a) a first agent selected from the group consisting of: medium chain triglyceride and a long chain triglyceride; and
  b) a second agent comprising a proton pump inhibitor or pharmaceutically or veterinary acceptable salt,
wherein the composition is adapted for sustained release of a therapeutically effective amount of the proton pump inhibitor to a subject in need thereof.

According to a second aspect of the invention, there is a composition comprising:
  a) a first agent selected from the group consisting of: a polymer, a medium chain triglyceride and a long chain triglyceride; and
  b) a second agent comprising a proton pump inhibitor or pharmaceutically or veterinary acceptable salt,
wherein the composition is adapted for sustained release of a therapeutically effective amount of the proton pump inhibitor.

The composition described above and in more detail below may be used in the method of the present invention described above.

In an embodiment of the invention, the proton pump inhibitor is selected from the group consisting of: rabeprazole, lansoprazole, tenatoprazole, omeprazole, esomeprazole and any pharmaceutically or veterinary analogs, enantiomers and polymorphs thereof and any pharmaceutically or veterinary equivalent salt thereof. Preferably the proton pump inhibitor is omeprazole and any pharmaceutically or veterinary analogs, enantiomers and polymorphs thereof and any pharmaceutically or veterinary equivalent salt thereof.

Omeprazole is a selective and irreversible proton pump inhibitor. It suppresses stomach acid secretion by specific inhibition of the H+/K+–ATPase system found at the secretory surface of gastric parietal cells. The irreversible binding of the active sulfenamide derivative of omeprazole to the proton pumps renders them unable to continue functioning. However, the pumps are replaced within the gastric parietal cells of the stomach approximately every 12-24 hours. The continuing efficacy of the present invention over at least two and preferably four to ten days shows that the injectable formulation must be slowly releasing omeprazole, and thus allowing omeprazole to continuously concentrate in the parietal cells providing a continuous supply of prodrug to be converted to the active sulfenamide that binds to and inhibits the new proton pumps as they are created.

Previously, oral formulations of proton-pump inhibitors such as omeprazole have been administered to horses as a 1-2 g daily oral dose, which is effective for a period of 12-24 hours.

The present invention uses a similar sized dose (1-2 g omeprazole per horse depending on size) but provides at least 2 days, up to 10 days or more, of gastric acid suppression leading to sustained maintenance of the preferred gastric pH. The present invention therefore provides an effective dose of a proton-pump inhibitor for a period of at least two days (48 hours) up to at least 10 days or more. Given the simple formulation of the present invention, this long acting effect is surprising. Omeprazole is quickly degraded in the body, particularly in the presence of free hydrogen ions. The formulation of the present invention, and its use in a method of intramuscular injection, allows the omeprazole to be protected from the aqueous environment of the body for a longer period of time, and release the active agent over days rather than hours.

It has been found that the present method may deliver the proton pump inhibitor over a period of time of at least 2 days. This means that the composition is acting like a slow release depot injection, without the presence of the combination of excipients generally associated with such a depot injection. Without being held to any theory, we believe the slow release rate of the present composition is a result of the particle size of the proton pump inhibitor. It is believed that the small particles of the proton pump inhibitor are retained within the triglyceride component of the composition, dissolving slowly and delaying the release of tissue fluid soluble proton pump inhibitor.

Preferably, the proton pump inhibitor has a particle size of between 150 μm and 25 μm, more preferably between 100 μm and 40 μm, preferably about 75 μm or less. It has been found that smaller particles of the proton pump inhibitor provide a slower and more sustained release profile. Preferably, the proton pump inhibitor with a particle size as discussed above is provided in a medium or long chain triglyceride. More preferably, the proton pump inhibitor with a particle size as discussed above is provided in a medium or long chain triglyceride first agent having a viscosity at 20° C. of between about 20 and 70 mPa·s, preferably between about 25 and 65 mPa·s, more preferably between about 27 and 55 mPa·s.

Proton pump inhibitors such as omeprazole are known to be chemically unstable when exposed to high temperatures, light and environments with low pH. Currently there are no ready to use solutions or suspensions of omeprazole for oral or parenteral use that have a commercially acceptable stability profile, and preparations for injection need to be prepared immediately before use. It is therefore a desired feature when developing a new product to ensure that a stable formulation can be demonstrated. The present invention provides stable composition of a proton pump inhibitor. The formulation is preferably stable for at least a time period selected from the group consisting of: 1 month, 2 months, 3 months, 4 months, 5 months, 6 months, 12 months, 2 years and 3 years. In a further embodiment, the composition is stable at a temperature selected from the group consisting of: 4° C., 25° C., 30° C. and 40° C. Preferably, the proton pump inhibitor composition is non-aqueous.

In one embodiment, the composition sustains the release of a therapeutically effective amount of the proton pump inhibitor in a subject over a period of time selected from the group consisting of: 1 day, 2 days, 3 days, 4 days, 5 days, 6 days, 1 week, 2 weeks, 3 weeks, 1 month, 2 months, 3 months, 4 months, 5 months, and 6 months.

In a further embodiment, the therapeutically effective amount detected in the subject's blood plasma is selected from the group consisting of: 1-10000 ng/ml, 10-5000 ng/ml, 50-2000 ng/ml, 500-1500 ng/ml, 100-400 ng/ml, 800-1200 ng/ml; and 900-1100 ng/ml.

In a further embodiment, the composition comprises a therapeutically effective amount of the proton pump inhibitor.

In a further embodiment, the concentration of proton pump inhibitor is selected from the group consisting of: from 1 mg/ml to 500 mg/ml, from 50 mg/ml to 200 mg/ml, 150 mg/ml and 100 mg/ml.

In a further embodiment, the first agent is a medium chain triglyceride (MCT), wherein at least two of the fatty acids have an aliphatic tail of 6-12 carbon atoms. Like all triglycerides, MCTs are composed of a glycerol backbone and three fatty acids. In the case of MCTs, two or three of the fatty acid chains attached to glycerol are of medium length. Examples of medium chain triglycerides include, but are not limited to: coconut oil, Miglyol®, Captex®, Neobee, Bergabest. Labrafac CC, and Myritol.

Preferably, the medium chain triglyceride is Miglyol® (e.g. Miglyol 812), or Captex® (e.g. Captex 355).

In a further embodiment, the first agent is a long chain triglyceride, preferably a vegetable oil rich in long chain fatty acids. Long-chain triglycerides are triglycerides wherein at least one of the fatty acids has an aliphatic tail of 13 or more carbon atoms. Examples of long chain triglycerides include, but are not limited to: safflower oil, soybean oil, peanut oil, linseed oil, olive oil, cotton seed oil, sunflower seed oil, almond oil, canola oil, castor oil, sesame oil, corn oil, palm oil.

Preferably, the long chain triglyceride is sesame oil or peanut oil.

Preferably, the medium or long chain triglyceride has a viscosity at 20° C. of between about 20 and 70 mPa·s, preferably between about 25 and 65 mPa·s, more preferably between about 27 and 55 mPa·s.

In a further embodiment, the concentration of the first agent is selected from the group consisting of: between 5-95% w/v, between 10-90% w/v, between 60-80% w/v, between 70-80% w/v, between 5-50% w/v, between 10-40% w/v; between 20-30% w/v and 25% w/v. Preferably it is between about 70-80% w/v.

In a further embodiment, the first agent may be PVP K30.

In a further embodiment, the first agent polymer is a poloxamer.

In a further embodiment, the polymer is a poloxamer selected from the group consisting of Poloxamer 101, 105, 108, 122, 123, 124, 181, 182, 183, 184, 185, 188, 212, 215, 217, 231, 234, 235, 237, 238, 282, 288, 331, 333, 334, 335, 338, 401, 402, 403, and 407.

In a further embodiment, the first agent has a surface tension of about 41 mN/m (41 dynes/cm) for a 0.1% aqueous solution of first agent at 25° C.

In a further embodiment, the composition is a liquid at 4° C. and is a gel at 37° C.

In a further embodiment, the composition has a viscosity between 1 cps and 10 cps at 4° C. and a viscosity of between 10,000 to 25,000 cps at 37° C.

In a further embodiment, the composition has a viscosity of about 5 cps at 4° C. and a viscosity of between about 10,000 to 25,000 cps at 37° C. In a further embodiment, the first agent is a liquid at 4° C. and a gel at 37° C. In a further embodiment, the first agent has viscosity between 0.5 cps and 50 cps at 4° C. and a viscosity of between 1000 to 50,000 cps at 37° C.

In a further embodiment, the first agent has viscosity between 1 cps and 10 cps at 4° C. and a viscosity of between 10,000 to 25,000 cps at 37° C. In a further embodiment, the first agent has viscosity of about 5 cps at 4° C. and a viscosity of between about 10,000 to 25,000 cps at 37° C.

In a further embodiment, the first agent has an amphiphilic structure.

In a further embodiment, the polymer is a triblock copolymer.

In a further embodiment, the polymer is a hydrophilic non-ionic surfactant.

In a further embodiment, the polymer is a copolymer of ethylene oxide and propylene oxide.

In a further embodiment, the polymer is a nonionic polyoxyethylene-polyoxypropylene copolymer surfactant.

In a further embodiment, the polyoxyethylene segment is hydrophilic while the polyoxypropylene segment is hydrophobic.

In a further embodiment, the composition comprises water. In a further embodiment, the concentration of water is selected from the group consisting of: between 50-95% w/v, between 60-90% w/v; between 70-80% w/v and 75% w/v.

In a further embodiment, the composition is non-aqueous.

In a further embodiment, the composition comprises a stabiliser. Preferably the stabiliser is an alkaline agent. More preferably the stabiliser is an amino acid, such as a basic amino acid. The presence of a stabiliser, such as a basic amino acid, assists in the protection of the proton pump (e.g. omeprazole) from the presence of free hydrogen ions in the environment, particularly an aqueous biological environment such as the intramuscular environment.

In a further embodiment, the ratio of the proton pump inhibitor to the stabiliser by weight is selected from the group consisting of: between 1:1 to 1:2; between 1:1.3 to 1:1.7; and 1:1.5.

In a further embodiment, the amino acid is selected from the group consisting of: arginine and lysine. Preferably, the amino acid is L-arginine.

In a further embodiment, the composition is sterile. The composition may be sterilized by dry heat, irradiation, or chemical sterilization. The composition preferably has a sterility assurance level of 10 to the minus six ($10^{-6}$), which equates to 1 non-sterile item per 1 million items sterilised. In a further embodiment, the composition has complete absence of detectable viable microorganisms.

In a further embodiment, the composition does not contain Tween 20.

In a further embodiment, the composition has a pH selected from the group consisting of: 7 to 8, 8 to 9, 9 to 10, 10 to 11, 11 to 12, 12 to 13; 11.1 to 11.9, 11.2 to 11.8; 11.3 to 11.7, 11.4 to 11.6; about 11; about 11.5.

In a further embodiment, the composition is stable for a time periods selected from the group consisting of: 1 month, 2 months, 3 months, 4 months, 5 months, 6 months, 12 months, 2 years and 3 years.

In a further embodiment, the composition is stable at a temperature selected from the group consisting of: 4° C., 25° C., 30° C. and 40° C.

In a third aspect, the invention is a pharmaceutical composition, preferably a veterinary pharmaceutical composition comprising the composition according to the second aspect of the invention.

In a fourth aspect, the invention is a dosage form, comprising the composition according to the second aspect of the invention, sealed in a container.

In a fifth aspect, the invention is a unit dosage form comprising the composition according to the second aspect of the invention, wherein the total amount of the proton pump inhibitor is selected from the group consisting of: between 1 mg and 10,000 mg; between 100 mg and 5,000 mg; between 200 and 4,000 mg; 300 mg, 400 mg, 500 mg, 600 mg, 700 mg, 800 mg, 900 m, 1000 mg, 1,500 mg, 2000 mg, and 3000 mg.

In a sixth aspect, the invention is a process for the manufacture of the composition according to the second aspect of the invention, said process comprising the steps of: (1) mixing the proton pump inhibitor and the first agent; and (2) dispensing the mixture into a container.

In a further embodiment, the subject is human, equine, canine, feline, porcine, bovine, ovine, camelid (member of the camel family which includes dromedary camel, Bactrian camels, llamas, alpacas, vicuñas and guanacos).

In a further embodiment, the subject is human, equine, canine, camelid.

In a further embodiment, the gastric ulcer is an ulcer selected from the group consisting of: stomach ulcer; duodenal ulcer, oesophageal ulcer. In a further embodiment, the gastric ulcer is a peptic ulcer.

In a further embodiment, the method treats or prevents, equine gastric ulcer syndrome, dyspepsia, peptic ulcer disease, gastroesophageal reflux disease (GORD), laryngopharyngeal reflux, erosive esophagitis, and Zollinger-Ellison syndrome. The equine gastric ulcer syndrome may be squamous gastric ulcer syndrome or equine glandular gastric ulcer syndrome.

The method of the present invention preferably treats or at least reduces the severity of squamous and glandular ulcers in horses more rapidly than oral proton pump inhibitor treatments. It has been found that the present method is effective in the treatment of squamous ulcers in about 14 days. The consensus on omeprazole treatment using traditional oral dosing is that approximately 70-80% of squamous ulcers will heal within a 28 day treatment period (see page 1295 of Sykes et al. (2015). *Journal of Veterinary Internal Medicine* 29(5): 1288-1299). Furthermore, the present method provides healing, of or at least a reduction in the severity of, glandular ulcer in about 14 days. The consensus statement found that only 25% of gastric ulcers had healed in 28-35 days using traditional oral dosing and the recommended treatment time is 8 to 12 weeks (see page 1295 of Sykes et al. (2015)).

In a further embodiment, the composition is adapted for a mode of administration selected from the group consisting of: intravenous, intramuscular; subcutaneous, and intraperitoneal injection. Preferably, the composition is adapted for administration by intramuscular injection In a further embodiment, the composition is administered using a method selected from the group consisting of: injection, diffusion pump.

In a further embodiment, the composition is administered intramuscularly to a muscle selected from the group consisting of neck (epaxial) muscles or pectoral muscles in the horse; vastus lateralis, deltoid, ventrogluteal and dorsogluteal muscles in humans, selected according to age and body condition.

In a further embodiment, the method does not irritate the site of administration in the subject. It has surprisingly been found that the present composition generally causes little or no irritation at the injection site. This aspect is important in dealing with subjects such as horses, and particularly racing horses. In a further embodiment, the method does not cause at the site of administration in the subject a reaction selected from the group consisting of: redness, bruising, hot to touch, pain, swelling, itching, stinging and burning.

In a further embodiment, the method does not cause a site reaction at the site of administration. In a further embodiment, the method does not irritate the site of administration in the subject to an irritation level greater than mild, selected from the group consisting of: MILD (Erythema only; edema or induration which is measurable but 30 mm or less in any one diameter) MODERATE (Edema or induration measuring greater than 30 mm and less than 120 mm in any one diameter); and SEVERE (Any reaction measuring more than 120 mm in any one diameter or any reaction accompanied by marked limitation of motion of the arm or marked axillary node tenderness), as described in McNeil, M. M., et al. (2007). "Short-term reactogenicity and gender effect of anthrax vaccine: analysis of a 1967-1972 study and review of the 1955-2005 medical literature." Pharmacoepidemiology and Drug Safety 16(3): 259-274.

In a further embodiment, the method results in the sustained release of a therapeutically effective amount of the proton pump inhibitor over a period of time selected from the group consisting of: 1 day, 2 days, 3 days, 4 days, 5 days, 6 days, 1 week, 2 weeks, 3 weeks, 1 month, 2 months, 3 months, 4 months, 5 months, and 6 months.

In a further embodiment, the method provides a minimum effective amount of the proton pump inhibitor in the subject's blood stream over a period of time selected from the group consisting of: 1 day, 2 days, 3 days, 4 days, 5 days, 6 days, 1 week, 2 weeks, 3 weeks, 1 month, 2 months, 3 months, 4 months, 5 months, and 6 months.

In a further embodiment, the method provides a minimum effective amount of the proton pump inhibitor in the subject's gastric parietal cells over a period of time selected from the group consisting of: 1 day, 2 days, 3 days, 4 days, 5 days, 6 days, 1 week, 2 weeks, 3 weeks, 1 month, 2 months, 3 months, 4 months, 5 months, and 6 months.

In a further embodiment, the minimum effective amount is selected from the group consisting of: 10 to 2000 ng/ml, 50 to 1000 ng/ml, 75 to 500 ng/ml and 100 to 250 ng/ml.

The concentration of formulation and injection volume may affect the absorption and release rate of proton pump inhibitor. In an oily suspension, drug particles need to reach the oil/water interface before they can be released into the surrounding environment. Preferably, the dose of the proton pump inhibitor is about 50 mg/ml in a volume of 40 ml (high blood concentration for short duration), about 100 mg/ml in about 20 ml (lower blood concentration and longer duration compared to 50 mg/mL), or about 200 mg/ml in about 10 ml (lowest blood concentration and longest duration).

In a further embodiment, the composition is administered using a dosing regimen selected from the group consisting of: once daily, every two days, every three days, every four days, every five days, every six days, twice weekly, once weekly, every two weeks, every three weeks, once monthly, every two months, every three months, every four months, every five months, and every six months.

In a further embodiment, the method administers to the subject a total amount of proton pump inhibitor selected from the group consisting of: between 0.1 mg/kg bodyweight (bwt) and 50 mg/kg bwt, between 2 mg/kg bwt and 10 mg/kg bwt, between 3 mg/kg bwt and 8 mg/kg bwt at each administration.

In a further embodiment, the method maintains the pH of the stomach above pH 4 for a time period selected from the group consisting of: for at least 15 hours in 24 hours; for at least 16 hours in 24 hours; for at least 17 hours in 24 hours; for at least 18 hours in 24 hours; for at least 19 hours in 24 hours; for at least 20 hours in 24 hours; for at least 21 hours in 24 hours; for at least 22 hours in 24 hours; for at least 23 hours in 24 hours; for 24 hours in 24 hours.

In a further embodiment, the method provides a $C_{max}$ selected from the group consisting of: 1-10000 ng/ml, 10-5000 ng/ml, 50-2000 ng/ml, 100-1500 ng/ml, 150-1200 ng/ml; 200-800 ng/ml, and 200 ng/ml.

In a further embodiment, the method provides a $T_{max}$ selected from the group consisting of: 15-600, 30-500, 45-400, 30-300 and 60-300 minutes.

In a further embodiment, the method provides a $AUC_{(0-infinity)}$ selected from the group consisting of: 4 to 4,000, 10 to 3,000, 50 to 2,000, 100 to 1,000 mcg/mL·min and 950 mcg/mL·min.

In a seventh aspect of the invention, the invention is a method of treating and/or preventing a disease or disorder in a subject in need thereof, said method comprising administering a therapeutically effective amount of the composition of the first aspect of the invention to the subject, wherein the disease is selected from the group consisting of: equine gastric ulcer syndrome, dyspepsia, peptic ulcer disease, gastroesophageal reflux disease, laryngopharyngeal reflux, erosive esophagitis, and Zollinger-Ellison syndrome.

In a further embodiment, the equine gastric ulcer syndrome is equine squamous gastric disease (ESGD) or equine glandular gastric disease (EGGD).

In an eighth aspect of the invention, the invention is a method of increasing the pH of the stomach of a subject, said method comprising administering the composition of the first aspect of the invention to a subject in need thereof.

In a ninth aspect of the invention, the invention is a method of maintaining the pH of the stomach of a subject at or above pH 4, said method comprising administering the composition of the first aspect of the invention to a subject in need thereof.

In a further embodiment, the pH is maintained above pH 4 for at least 16 hours per day, for at least 5 days.

In a tenth aspect of the invention, the invention is a kit, comprising the composition of the first aspect sealed in a container, further comprising an administration means and a label. In a further embodiment, the administration means is a syringe for injection. In a further embodiment, the container is sealed to prevent contamination. In a further embodiment, the composition has a sterility assurance level of 10 to the minus six ($10^{-6}$), which equates to 1 non-sterile item per 1 million items sterilised. In a further embodiment, the label comprises the claim that the composition treats or prevents gastric ulcers.

In an eleventh aspect of the invention, the invention is the use of the composition of the first aspect of the invention in the manufacture of a medicament for treating and/or preventing gastric ulcers.

In a further embodiment, the composition comprises:

TABLE 1

| Ingredient/Parameter | Quantity/Concentration |
| --- | --- |
| Omeprazole | 100 mg/mL |
| Sesame oil | to volume |
| Drug: L-arginine | 1:1.5 |
| Total dose of omeprazole administered to subject | 2,000 mg |
| Method of administration | Intramuscular injection |
| Dosing regimen | 1 dose once weekly |
| Effect | Maintains stomach pH at 4 or above for at least 16 hours of 24 each day, for at least 5 days. |
| Subject | Horse with stomach ulcer |
| Minimum effective amount in blood plasma to achieve effect | 20 ng/ml |
| Cmax | 200 ng/ml |
| Tmax | 30-300 minutes |
| AUC | 950 mcg/mL · min |
| Further features | gastric pH increases above 4 within 6 h of injection increase in gastric pH is independent of prandial status |

The composition of the invention may further comprise an excipient selected from the group comprising, but not limited to, binders and compression aids, coatings and films, colouring agents diluents and vehicles disintegrants, emulsifying and solubilising agents, flavours and sweeteners, repellents, glidants and lubricants, plasticisers, preservatives, propellants, solvents, stabilisers, suspending agents and viscosity enhancers. In an embodiment of the invention, the composition further comprises a basic substance such as L-arginine. It will be understood that such excipients may result in a change of the pH of the composition.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

DESCRIPTION OF EMBODIMENTS

General

Before describing the present invention in detail, it is to be understood that the invention is not limited to particular exemplified methods or compositions disclosed herein. It is also to be understood that the terminology used herein is for the purpose of describing particular embodiments of the invention only, and is not intended to be limiting.

All publications referred to herein, including patents or patent applications, are incorporated by reference in their entirety. However, applications that are mentioned herein are referred to simply for the purpose of describing and disclosing the procedures, protocols, and reagents referred to in the publication which may have been used in connection with the invention. The citation of any publications referred to herein is not to be construed as an admission that the invention is not entitled to antedate such disclosure by virtue of prior invention.

In addition, the carrying out of the present invention makes use of, unless otherwise indicated, conventional veterinary clinical techniques within the skill of the art. Such conventional techniques are known to the skilled worker.

As used herein, and in the appended claims, the singular forms "a", "an", and "the" include the plural unless the context clearly indicates otherwise.

Unless otherwise indicated, all technical and scientific terms used herein have the same meanings as commonly understood by one of ordinary skill in the art to which this invention belongs. Although any materials and methods similar to, or equivalent to, those described herein may be used to carry out the present invention, the preferred materials and methods are herein described.

The invention described herein may include one or more ranges of values (e.g. size, concentration, dose etc). A range of values will be understood to include all values within the range, including the values defining the range, and values adjacent to the range that lead to the same or substantially the same outcome as the values immediately adjacent to that value which define the boundary of the range.

The phrase "therapeutically effective amount" as used herein refers to an amount sufficient to maintain the pH of the stomach above a pH of 4 for a time period selected from the group consisting of: for at least 15 hours in 24 hours; for at least 16 hours in 24 hours; for at least 17 hours in 24 hours; for at least 18 hours in 24 hours; for at least 19 hours in 24 hours; for at least 20 hours in 24 hours; for at least 21 hours in 24 hours; for at least 22 hours in 24 hours; for at least 23 hours in 24 hours; for 24 hours in 24 hours. The phrase "therapeutically effective amount" as used herein also refers to an amount sufficient to maintain the pH of the stomach above a pH of 4 for at least 16 hours in 24 hours for at least 5 days, for at least 6 days, for at least 7 days in one week. The phrase "therapeutically effective amount" as used herein also refers to an amount sufficient to at least partially treat or prevent a gastric ulcer. The term "therapeutically effective amount" as used herein, refers to a nontoxic but sufficient amount of the composition to provide the desired biological, therapeutic, and/or prophylactic result. An effective amount in any individual case may be determined by one of ordinary skill in the art using routine experimentation. In relation to a pharmaceutical or veterinary composition, effective amounts can be dosages that are recommended in the modulation of a diseased state or signs or symptoms thereof. Effective amounts differ depending on the pharmaceutical or veterinary composition used and the route of administration employed. Effective amounts are routinely optimized taking into consideration various factors of a particular patient, such as age, weight, gender, etc and the area affected by disease or disease causing microorganisms.

The term "omeprazole" as used herein refers to the compound having the chemical name 6-methoxy-2-[(4-methoxy-3,5-dimethylpyridin-2-yl)methanesulfinyl]-1H-1,3-benzodiazole (also known as 5-methoxy-2-{[(4-methoxy-3,5-dimethyl-2-pyridinyl)methyl]sulfinyl}-1H-benzimidazole) and chemical structure:

The term "esomeprazole" as used herein refers to the compound having the chemical name (S)-5-Methoxy-2-[(4-methoxy-3,5-dimethylpyridin-2-yl)methylsulfinyl]-3H-benzoimidazole (also known as 5-methoxy-2-{(S)-[(4-methoxy-3,5-dimethyl-2-pyridinyl)methyl]sulfinyl}-1H-benzimidazole) and chemical structure:

Pharmaceutically or veterinary acceptable salts include salts which retain the biological effectiveness and properties of the compounds of the present disclosure and which are not biologically or otherwise undesirable. In many cases, the compounds disclosed herein are capable of forming acid and/or base salts by virtue of the presence of amino and/or carboxyl groups or groups similar thereto. Pharmaceutically or veterinary acceptable base addition salts can be prepared from, inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as by way of example only, alkyl amines, dialkyl amines, trialkyl amines, substituted alkyl amines, di(subsrituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diary amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

The pharmaceutically or veterinary acceptable salts of the compounds useful in the present disclosure can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences. 17th ed., Mack Publishing Company, Easton, Pa. (1985), p. 1418, the disclosure of which is hereby incorporated by reference. Examples of such pharmaceutically or veterinary acceptable salts are the iodide, acetate, phenyl acetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, γ-hydroxybutyrate, β-hydroxybutyrate, butyne-I,4-dioate, hexyne-I,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, merhanesulfonate, naphthalene-I-sulfonate, naphthalene-2-sulfonate, p-toluenesulfonate, xylenesulfonate, tartarate, and the like.

Throughout this specification, unless the context requires otherwise, the word "comprise" or variations such as "comprises" or "comprising", will be understood to imply the inclusion of a stated integer or group of integers but not the exclusion of any other integer or group of integers.

EXAMPLE 1

Preparation of an In-Situ Gel Based Intramuscular Injectable Formulation for Omeprazole The formulation developed in this example has the following constituents.

TABLE 2

| Ingredient | Quantity |
|---|---|
| Omeprazole (OMP) | 150 mg/mL (1.8 g) |
| Poloxamer 407 solution | 25% w/v (3.0 g added to 12 ml of water) |
| Drug: L-arginine | 1:1.5 |
| Autoclaved Water | Quantity Sufficient |

Materials and Methods

A total of 3.0 g of Poloxamer 407 was added to 12 ml of autoclaved water and stored in a refrigerator (4° C.) to dissolve the poloxamer and convert the solution to a clear transparent liquid. A total of 1.8 g of OMP (lot #111101, Cleo Shang) and 2.7 g L-arginine in the ratio of 1:1.5 (OMP:L-arginine) were added to the above prepared transparent liquid and mix uniformly by vortex for 10 to 15 minutes. Vials were filled with the preparation and sterilized using gamma irradiation at 25 kGy. The intramuscular injectable formulation was stored at 4° C. and stored in an ice bucket immediately prior to injection.

EXAMPLE 2

Further Examples of Suitable Formulations for Intramuscular Injectable

In addition to the formulation of Example 1, the following formulations were also prepared:

TABLE 3

| Formulation Code | Vehicle | L-Arginine (mg/ml) | OM00PC003 (Omeprazole - mg/ml) | Comments |
|---|---|---|---|---|
| F4 OM03IM025 | Peanut oil (Long chain triglyceride; Non-aqueous) | 150 | 100 | 16 G/18 G needles can be used |
| F3 OM03IM026 | Miglyol 812 (medium chain triglyceride; Non-aqueous) | 150 | 100 | |

TABLE 3-continued

| Formulation Code | Vehicle | L-Arginine (mg/ml) | OM00PC003 (Omeprazole - mg/ml) | Comments |
|---|---|---|---|---|
| F1 OM03IM029 | Sesame oil (Long chain triglyceride; Non-aqueous) | 150 | 100 | |
| F6 OM03IM033 | Captex 355 (medium chain triglyceride; Non-aqueous) | 150 | 100 | |
| F5 | PVP K30 (Aqueous) | 150 | 100 | Needle 14 G |

Formulations containing 200 mg/ml of omeprazole were also prepared.

Materials and Methods

The required quantities of sesame oil, peanut oil, Miglyol 812, Captex 355 were measured and allocated. Omeprazole was filtered through a 250 mesh sieve to provide uniform particles and uniformity in the formulations. L-arginine was also filtered through a 150 mesh sieve to provide uniform particles. L-arginine is added to the above-mentioned matrices while stirring on a magnetic stirrer for 30 minutes. Omeprazole is added to the mixture while stirring on a magnetic stirrer for 30 minutes. The ratio of omeprazole to L-arginine in the final mixture was 1:1.5. The mixture was added to a container, sealed and sterilized by gamma irradiation (25 kGy).

Results

Following intramuscular injection of horses all formulations were well tolerated, induced no detectable pain upon injection and no adverse site or systemic reactions were observed in treated horses.

EXAMPLE 3

Figure 1:
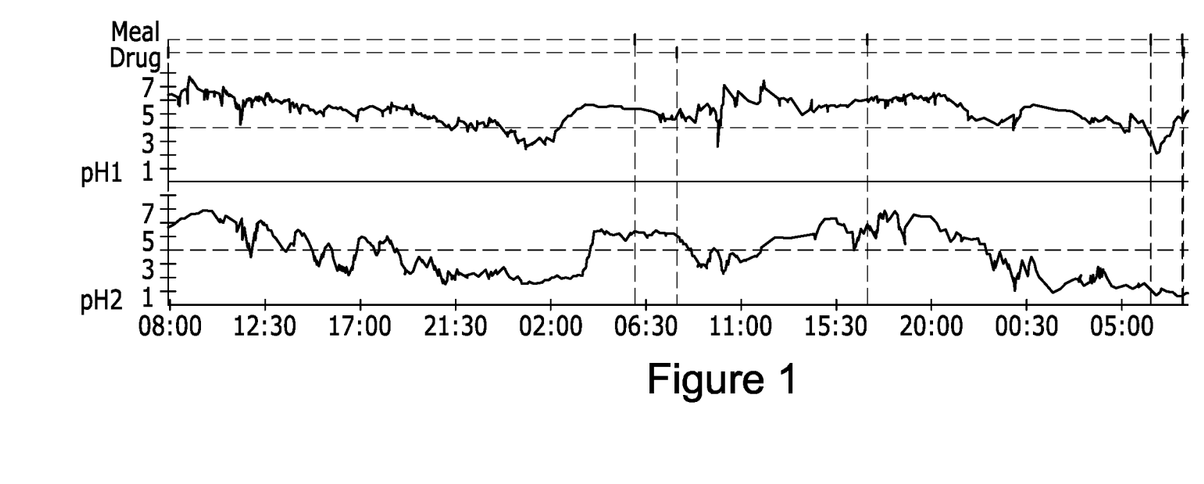
FIG. 1 presents a 48 h continuous trace of intragastric pH in a horse receiving 4 mg/kg of omeprazole (GastroGard®, Merial) by mouth once per day (8 am). In the lower trace labelled "pH 2" the intra-gastric pH is maintained above the critical threshold of 4 for only 50% of the time.

Investigation into the Long Acting Formulation of Omeprazole in a Single Healthy Horse A previous report (Merritt et al 2003) and preliminary investigations by the research group have indicated that the duration of intragastric acid suppression achieved with currently available forms of omeprazole may be a short as 12 hours. A 48 h continuous trace is presented in FIG. 1.

The duration of acid suppression required for healing of gastric ulceration in humans is a minimum of 16 hours per day (Bell et al 1992). These findings suggest that the currently available formulations of omeprazole may be inadequate for this purpose. To address this, a long acting injectable formulation of omeprazole has been developed. This report details the preliminary investigations into the efficacy of the formulation.

Materials and Methods

A 10 year old, 550 kg thoroughbred gelding was instrumented with a percutaneous gastrostomy (PEG) tube using a modification of the technique previously reported by Toth et al. At 8 am on day 0 a pH probe was inserted retrograde into the tube to a known distance and connected to a data monitor to allow continuous measurement of pH for the following 23 hour period. At 7 am each subsequent morning the probe was removed, recalibrated and replaced to begin measurement at 8 am. A baseline trace was taken on Day 0 and the medication prepared in Example 1 was administered by intramuscular injection at 8 am on day 1. A total of 15 ml of the medication was injected using a syringe into the neck muscle of the horse providing a total dose of OMP of 2250 mg. During the study the horse was fed good quality oaten/rye grass hay ad libitum.

Results

The injection was well tolerated and no local side effects were observed. No systemic side effects were observed and the horse remained clinically normal during the course of the project. The % time spent above a pH 4 and mean pH for each of the two intragastric pH probes is shown in Table 4 below.

TABLE 4

| | Day 0 | Day 1 | Day 2 | Day 3 | Day 4 | Day 5 | Day 6 | Day 7 | Day 8 |
|---|---|---|---|---|---|---|---|---|---|
| % Time pH > 4 within each day | | | | | | | | | |
| Probe 1 | 0.2 | 99.9 | 100 | N/A | 97.3 | 98.4 | 99.1 | 80.8 | 61.0 |
| Probe 2 | 0.1 | 84.0 | 99.5 | N/A | 96.3 | 98.9 | 99.5 | 56.7 | 37.9 |
| Mean daily gastric pH | | | | | | | | | |
| Probe 1 | 1.95 | 5.90 | 5.53 | N/A | 5.61 | 5.50 | 5.37 | 4.80 | 4.21 |
| Probe 2 | 1.88 | 5.87 | 5.59 | N/A | 5.50 | 5.63 | 5.55 | 4.17 | 3.42 |

Note:
Day 3 results were not available due to a technical error

Figure 2:
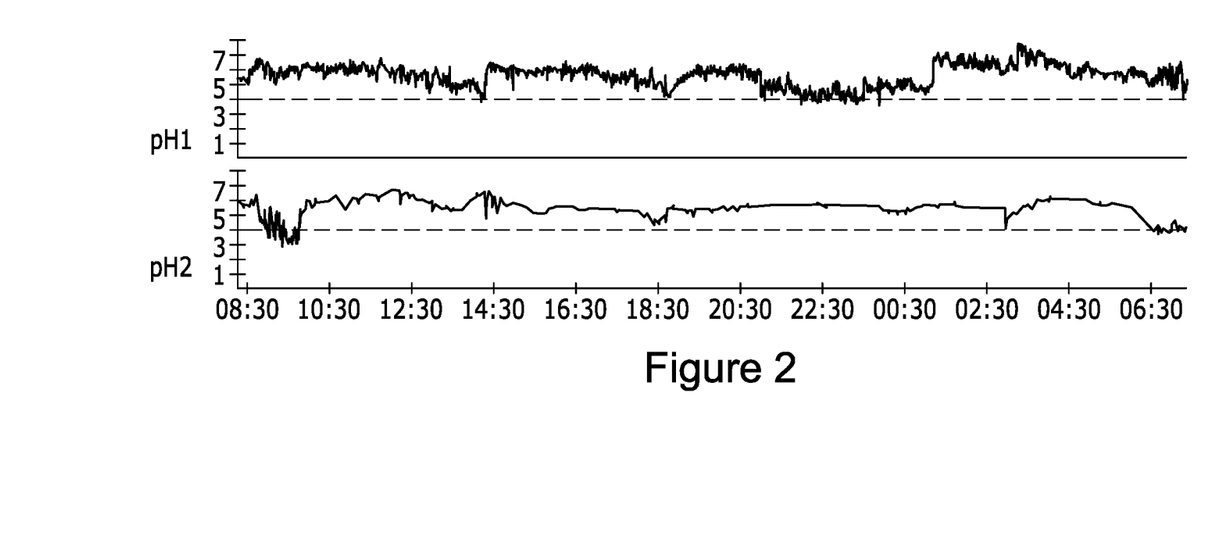
FIG. 2 is a trace from day 4 and demonstrates the high pH maintained on both probes throughout the study period.

On day 0, the pretreatment control day, the gastric contents were highly acidic the vast majority of the time and the mean pH of 1.88-1.95 reflects this. On day 1 following treatment, a rapid increase in pH was observed and the effect was maintained through to and including day 6. On day 7 the mean pH began to drop and the time above a pH of 4 decreased for both probes. This is consistent with the effects of the drug dissipating. By day 8 these effects continued towards pretreatment values. The trace from day 4 is presented in FIG. 2.

The results of this pilot investigation provide evidence that the novel formulation provides potent acid suppression for approximately 7 days. The magnitude and duration of acid suppression obtained significantly exceeds that achieved with current omeprazole formulations and dosing regimens.

EXAMPLE 4

Figure 3:
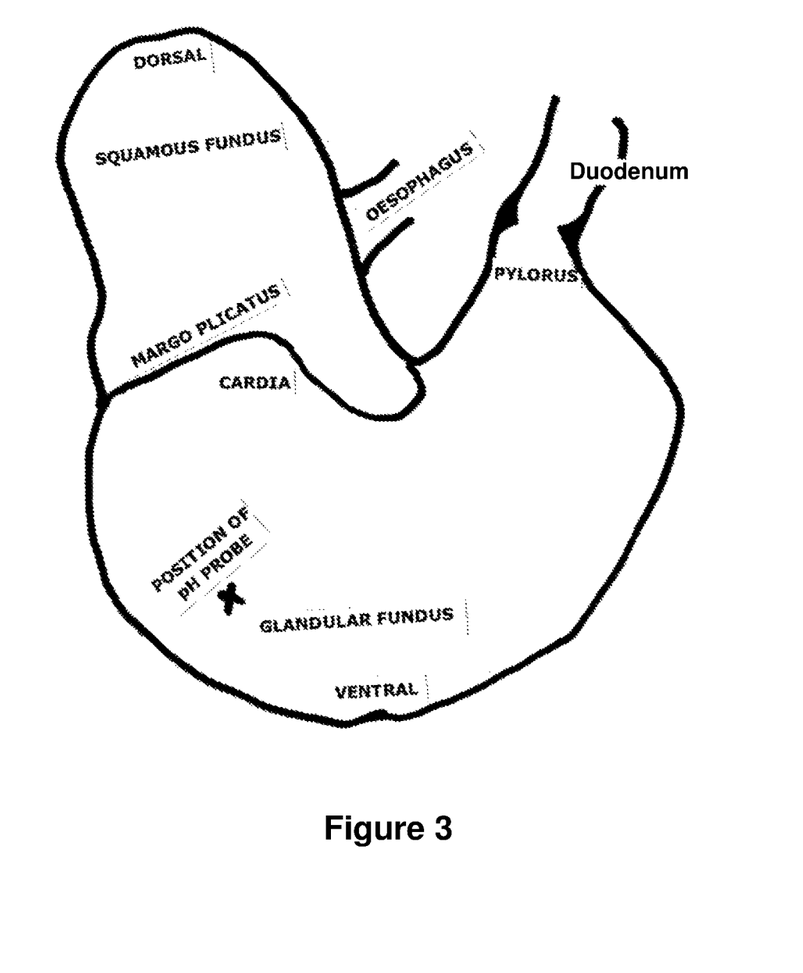
FIG. 3 presents a drawing of the location of pH probes in the ventral glandular fundus of the horse. probe 1 positioned ~1 cm from the mucosal surface, probe 2 freely within ingesta. (Adapted from Sykes et al 2015a,b)

Investigation into a Novel Long Acting Formulation of Omeprazole in Six Healthy Horses The aim of this study was to investigate the ability of novel formulations of omeprazole to suppress gastric acid production over a period of up to 1 week following intramuscular injection in healthy horses.
Materials and Methods
Horses Healthy Thoroughbred horses aged 7 to 15 years were used. Horses were housed in 16 m² stables and bedded on wood shavings throughout the study. Horses were feed ad libitum rye grass/lucerne hay that was supplemented with a commercial feed pellet as required to maintain body condition throughout the study period unless otherwise dictated by the diet under investigation. Each horse was instrumented with a percutaneous gastrotomy tube (PEG) (see FIG. 3, adapted from Sykes et al 2015b). The location of the PEG tube was confirmed by gastroscopy to be within the ventral glandular fundus approximately 10-15 cm below the margo plicatus adjacent to the lesser curvature in each horse.
Gastric pH Measurement Once adapted to their respective diets the intra-gastric pH of each horse was monitored for a period of 10 consecutive days. To achieve this; the pH probe was attached to a continuous data logger (Zephr pH) and calibrated prior to placement each day according to the manufacturer's instructions. The probe was then inserted a previously determined distance and secured as previously described (Sykes et al 2015b). Data recording commenced at 7:30 am and continued until 6:30 am the following day (23 hours). Mean, median, minimum and maximum pH and the % time below a pH of 4 was reported directly from the data logger's software program. Baseline data was recorded on day 0 with the medication administered at 7:30 am on day 1.
Omeprazole Formulation.

Figure 4:
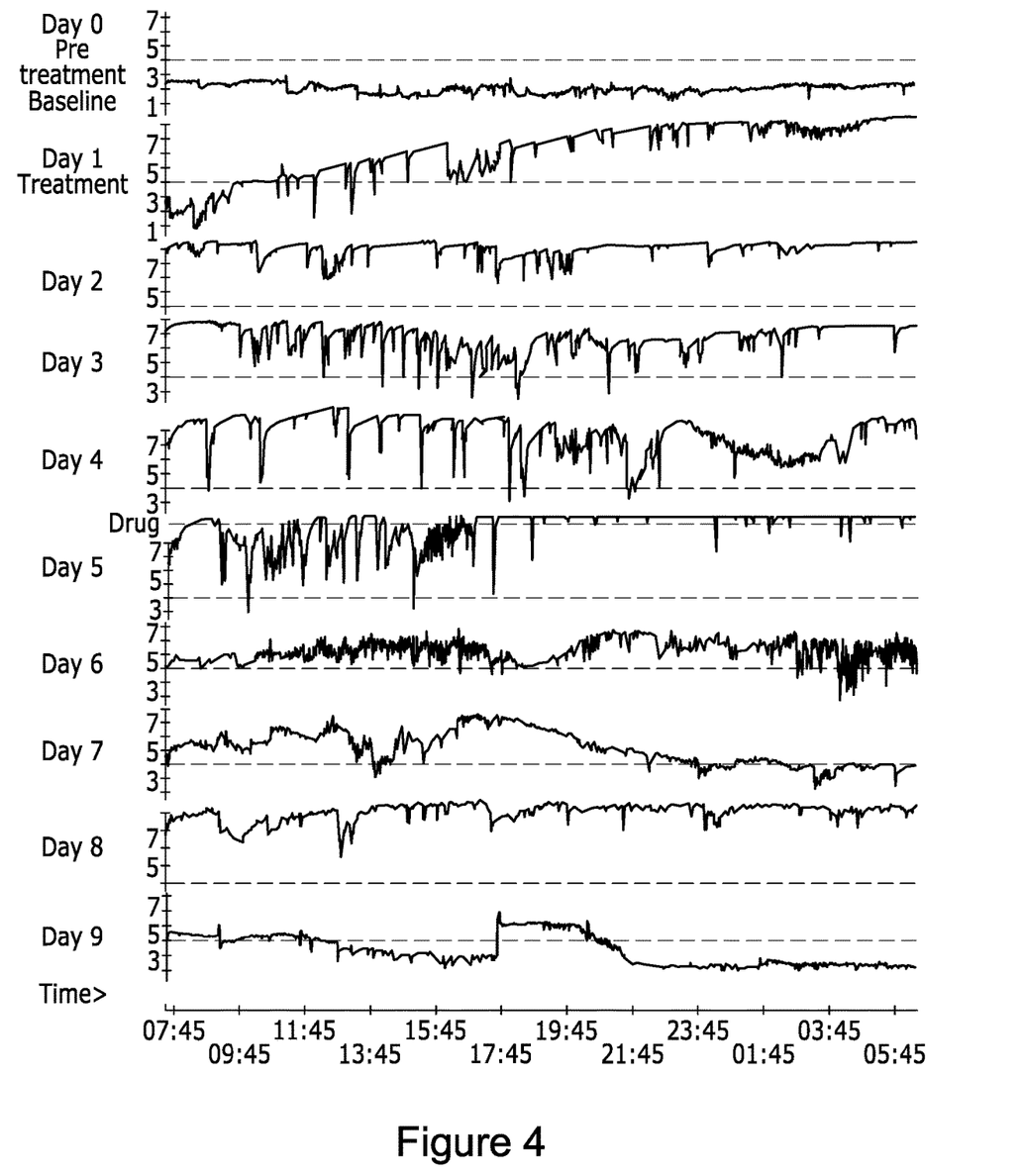
FIG. 4 presents a graph of the continuous daily pH record, Days 0-9, following omeprazole injection in a single horse (pH record from channel 1 only presented)

A baseline trace was taken on Day 0 and the medication ('F3" from Example 2: Miglyol 812, 100 mg/ml omeprazole, 150 mg/ml L-arginine) was administered by intramuscular injection at 7:30 am on Day 1. A total of 20 ml of the medication was injected using a syringe into the neck muscle of the horse subjects providing a total dose of OMP of 2,000 mg.
Results To illustrate the observations made during assessment, FIG. 4 presents the record of gastric pH recorded in one typical horse receiving formulation F3 from Example 2.

Prior to treatment with intramuscular omeprazole, the gastric pH recorded by channel 1 remains well below a pH of 4; in fact the median pH over the 23 h recording period was 2.01. The horse was treated at 7:30 am on Day 1 and the pH begins to rise within an hour and is at, or above, a pH of 4 from the second post treatment hour.

Figure 5:
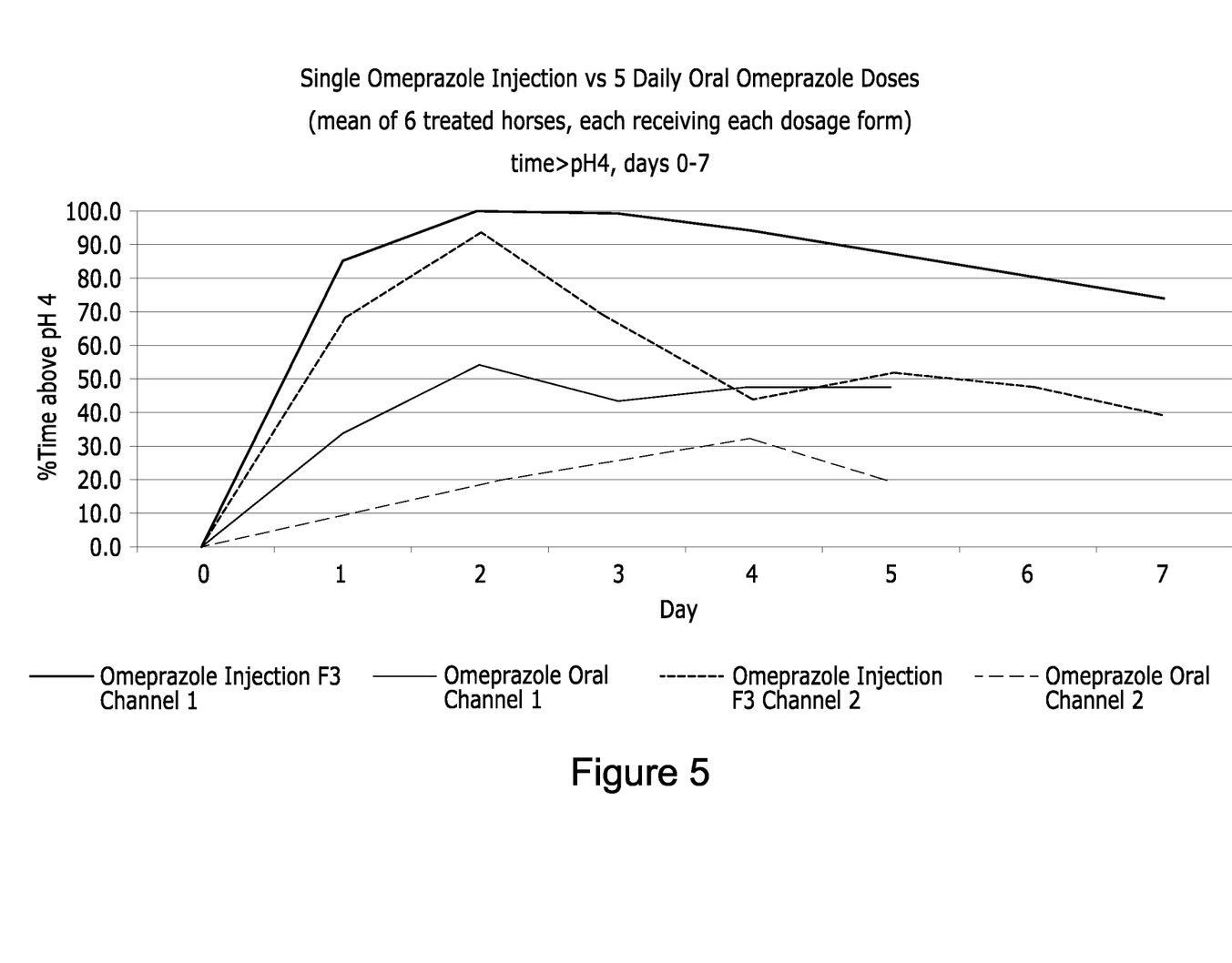
FIG. 5 presents a graph of the mean results from 6 horses following a single omeprazole injection of formulation F3 compared with daily omeprazole oral paste (Gastrogard) and presents the percentage of time above pH 4.
Figure 6:
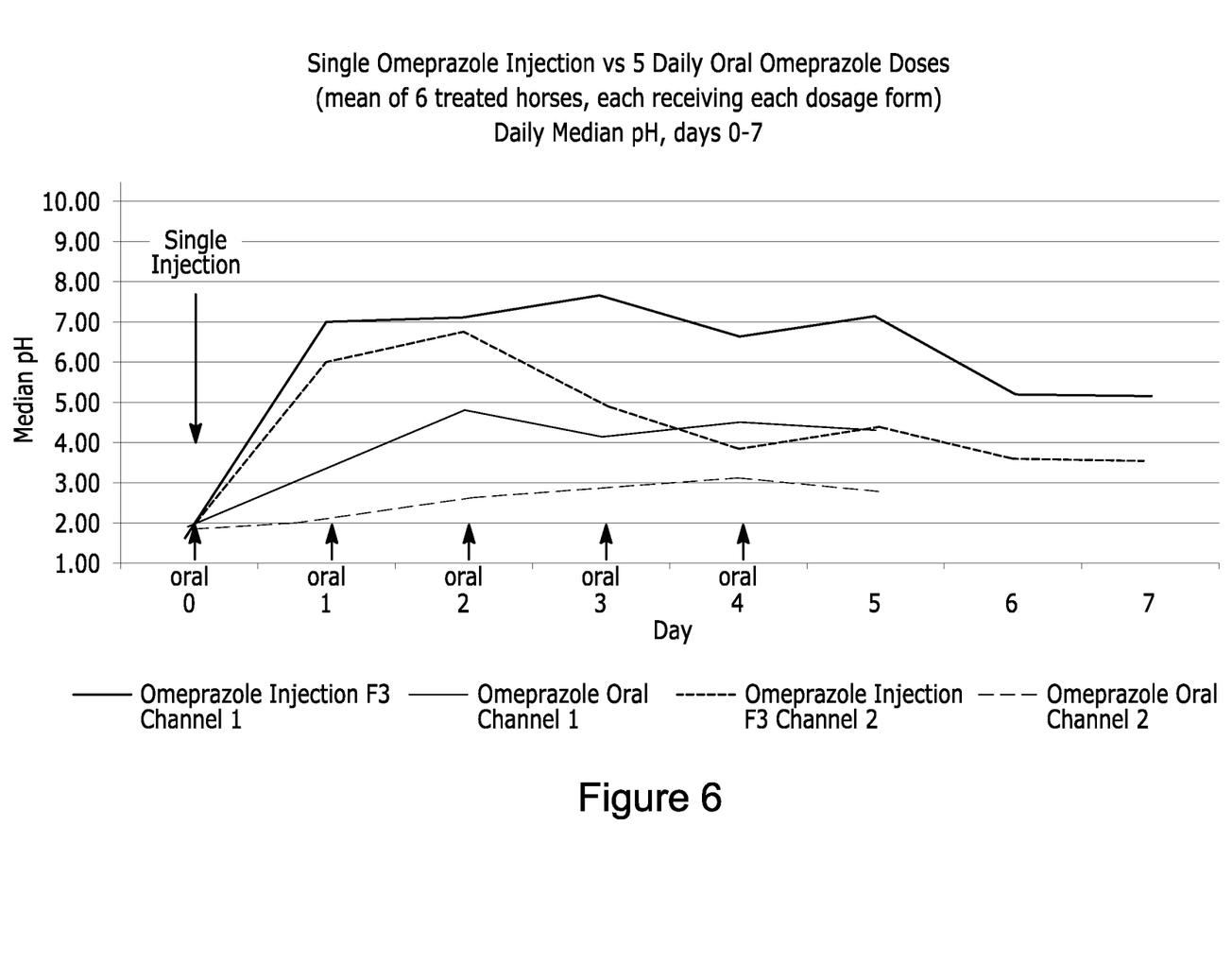
FIG. 6 presents a graph of the mean results from 6 horses following single omeprazole injection (F3) compared with daily omeprazole oral paste (Gastrogard) and presents the median daily pH.

The impact of intramuscular omeprazole on gastric pH can be appreciated by examining two important indices; the % time that gastric pH exceeds 4 (a widely accepted threshold required for ulcer healing), and the median daily pH (as calculated from the continuous daily recording). It is particularly relevant to compare the gastric pH response following omeprazole injection with the response following the current clinical standard treatment of daily oral omeprazole. FIGS. 5 and 6 present these indices for six horses on an identical high fibre hay diet receiving omeprazole (as Gastrogard® Oral Paste) 4 mg/kg orally once daily for 5 consecutive days.

Key differences between a single omeprazole injection and daily oral omeprazole include the fact that following daily oral administration the % time above a pH of 4 is 47.3% for channel 1 and only 19.5% for channel 2 at the fifth day (the time at which steady state conditions are reached). By contrast, following a single omeprazole injection the average time above a pH of 4 for days 1 to 7 inclusive was 88.8% for channel 1 and 58.8% for channel 2.

Furthermore, the median daily pH for oral omeprazole is 4.3 and 2.8 for channels 1 and 2, respectively, on Day 5, compared with a median daily pH over days 1 to 7 inclusive for the omeprazole injection of 6.6 and 4.7 for channels 1 and 2, respectively.

EXAMPLE 5

Investigation into an Injectable Long Acting Formulation of Omeprazole in Twenty Three Horses With Gastric Ulcers Methodology A pilot study in Thoroughbred horses has been carried out using formulation 'F3' from Example 2 (miglyol 812, 100 mg/ml omeprazole, 150 mg/ml L-arginine). The study involves gastroscopy of horses on Day 0 and selection of those with squamous and/or glandular ulcers for inclusion. Selected horses had ulcer grades recorded and received a 20 mL intramuscular injection in the musculature of the neck on Day 0 and a second injection on Day 7 in the contralateral musculature. On Day 14 gastroscopic inspection of the stomach of each treated horse was undertaken and ulcers graded.

TABLE 5

Squamous Ulcer Healing

| Horse ID | Age years | Sex | Weight kg | Squamous Ulcers[#] Grade (/4) | |
|---|---|---|---|---|---|
| | | | | Day 0 | Day 14/16 |
| L | 2 | Mare | 465 | 2 | 0 |
| C | 4 | Mare | 490 | 2 | 0 |
| D | 4 | Mare | 500 | 2 | 0 |
| B | 5 | Mare | 510 | 2 | 0 |
| S | 4 | Gelding | 530 | 2 | 0 |
| I | 4 | Mare | 545 | 2 | 0 |
| R | 5 | Gelding | 570 | 2 | 0 |
| T | 5 | Gelding | 580 | 2 | 0 |
| J | 5 | Mare | 590 | 2 | 0 |
| Q | 5 | Mare | 450 | 3 | 0 |
| N | 5 | Mare | 470 | 3 | 0 |
| F | 5 | Gelding | 475 | 3 | 0 |
| O | 7 | Gelding | 490 | 3 | 0 |
| E | 5 | Mare | 495 | 3 | 0 |
| H | 5 | Gelding | 550 | 3 | 0 |
| A | 5 | Gelding | 560 | 3 | 0 |
| G | 5 | Gelding | 455 | 4 | 0 |
| P | 7 | Gelding | 490 | 4 | 0 |
| K | 7 | Gelding | 495 | 4 | 0 |

TABLE 5-continued

Squamous Ulcer Healing

| Horse ID | Age years | Sex | Weight kg | Squamous Ulcers# Grade (/4) Day 0 | Day 14/16 |
|---|---|---|---|---|---|
| U | 6 | Gelding | 495 | 4 | 0 |
| M | 6 | Gelding | 540 | 4 | 0 |
|   |   |   | Median | 3 | 0 |

Squamous Ulcer Grading Scale
0 - The epithelium is intact and there is no appearance of hyperkeratosis
1 - The mucosa is intact, but there are areas of hyperkeratosis
2 - Small, single or multifocal lesions
3 - Large single or extensive superficial lesions
4 - Extensive lesions with areas of apparent deep ulceration

TABLE 6

Glandular Ulcer Healing

| Horse ID | Age y | Sex | Weight kg | Day 0 | Day 0 Description | Day 14 | Day 14 or 16 Description |
|---|---|---|---|---|---|---|---|
| 3 | 5 | Gelding | 475 | 1 | Moderately severe tiger striping throughout pyloric antrum with roughened epithelium | 0 |   |
| 8 | 7 | Gelding | 490 | 1 | Moderate hyperaemia with roughened mucosa | 0 | Slight hyperaemia with smooth mucosa |
| 2 | 5 | Mare | 495 | 1 | Ventral antral lesion x 1 | 0 |   |
| 4 | 7 | Gelding | 495 | 1 | Ventral antral lesions x 2 | 0 |   |
| 12 | 6 | Gelding | 495 | 1 | Ventral antral lesion x 1 | 0 |   |
| 6 | 5 | Gelding | 540 | 1 | Moderately severe tiger striping throughout pyloric antrum with roughened epithelium | 0 |   |
| 7 | 6 | Gelding | 540 | 1 | Moderately severe single ventral linear lesion in pyloric antrum | 0 |   |
| 1 | 5 | Gelding | 560 | 1 | 3 x small moderately severe focal lesions in pyloric antrum | 0 |   |
| 11 | 5 | Gelding | 580 | 1 | Moderately severe single ventral linear lesion in pyloric antrum | 0 |   |
| 9 | 5 | Mare | 450 | 2 | Single, large (3 x 7 cm), severe ventral linear lesion in pyloric antrum | 1 | No change in size but less severe with granulated appearance |
| 5 | 5 | Gelding | 490 | 2 | Tiger striping plus 3 focal lesions | 1 | No tiger stripping. Superficial linear lesions x 2 |
| 10 | 5 | Gelding | 570 | 2 | Tiger striping with linear ulcers on top + 3 x deep focal lesions | 1 | Single ventral linear lesion - granulated |

Glandular Ulcer Grading Scale
0 - normal mucosa with no evidence of loss of mucosal integrity, grade
1 - mild-moderate lesion(s) present with evidence of loss of mucosal integrity, and grade
2 - severe lesion(s) present with evidence of loss of mucosal integrity Based on Day 14 observations of 23 horses in a pilot study of omeprazole injection, the rate and extent of healing of gastric ulcers appears more rapid than ulcer healing following daily oral treatment of horses with omeprazole.

Injectable omeprazole is effective in the treatment of squamous ulcers in all horses tested in 14 days. The consensus on omeprazole treatment using traditional oral dosing is that approximately 70-80% of squamous ulcers will heal within a 28 day treatment period (see page 1295 of Sykes et al. (2015). *Journal of Veterinary Internal Medicine* 29(5): 1288-1299).

The glandular results represent the first time such rapid improvement has been observed with any intervention. The consensus statement is that only 25% of gastric ulcers had healed in 28-35 days using traditional oral dosing and the recommended treatment time is 8 to 12 weeks (see page 1295 of Sykes et al. (2015)). However, the present injectable formulation shows healing or at least reduction in ulcer severity in all horses after 14 days.

EXAMPLE 6

Stability of Omeprazole Formulations

Omeprazole is known to be chemically unstable when exposed to high temperatures, light and environments with low pH. Currently there are no ready to use solutions or suspensions of omeprazole for oral or parenteral use that have a commercially acceptable stability profile and preparations for injection need to be prepared immediately before use. It is therefore a desired feature when developing a new product to ensure that a stable formulation can be demonstrated. A stability study has been conducted with the omeprazole injection formulations of the present invention.
Methodology Formulations F1, F3, F4 and F5 described in Example 2 were prepared and filled into 12 mL amber glass vials. One half the number of the filled vials were subjected to gamma irradiation at 25 kGy to render the product sterile while the remaining vials of each batch was retained without irradiation. Each of the products were divided and filled vials were stored according to ICH stability recommendations in stability cabinets maintained at either 4° C., 25° C./60% relative humidity (RH), or at 40° C./75% RH. Following laboratory scale manufacture and gamma irradiation as appropriate, a sample of each batch was taken for analysis of omeprazole content by a validated HPLC method. Samples were taken from each stability cabinet at 1, 3 and 6 months for HPLC analysis. At the 6 month assessment the most stable formulation was selected for ongoing further storage and stability assessment.

Results

A summary of the results of the storage and analysis of 4 formulations of omeprazole injection are presented in the following table.

| Formulation | Gamma Irradiation kGy | Storage Conditions deg C./RH | Omeprazole Content mg/100 mL | | | | | |
|---|---|---|---|---|---|---|---|---|
| | | | Day 0 | Month 1 | Month 3 | Month 6 | Month 9 | Month 12 |
| F3 Medium Chain Triglycerides | 0 | 4° C. | 105.62 | 103.16 | 105.23 | 98.71 | 101.2 | 98.51 |
| | | 25° C./60% | 105.99 | 99.98 | 107.34 | 96.48 | 101.05 | 97.26 |
| | | 40° C./75% | 102.28 | 101.04 | 102.80 | 95.51 | 100.51 | — |
| | 25 | 4° C. | 100.14 | 100.09 | 102.28 | 100.89 | 100.74 | 96.51 |
| | | 25° C./60% | 103.19 | 102.97 | 99.02 | 100.56 | 100.56 | 95.26 |
| | | 40° C./75% | 104.24 | 105.85 | 96.61 | 99.69 | 98.89 | — |
| F1 Sesame oil | 0 | 4° C. | 103.29 | 102.04 | 104.40 | 95.26 | — | |
| | | 25° C./60% | 106.50 | 105.23 | 110.90 | 94.83 | — | |
| | | 40° C./75% | 108.56 | 99.95 | 108.83 | 94.90 | — | |
| | 25 | 4° C. | 102.94 | 100.40 | 100.72 | 95.51 | — | |
| | | 25° C./60% | 107.15 | 110.81 | 101.08 | 96.73 | — | |
| | | 40° C./75% | 106.42 | 109.10 | 98.59 | 96.52 | — | |
| F4 Peanut oil | 0 | 4° C. | 105.89 | 100.95 | 108.20 | 97.9 | — | |
| | | 25° C./60% | 106.27 | 101.35 | 109.23 | 95.97 | — | |
| | | 40° C./75% | 108.40 | 100.92 | 109.48 | 94.83 | — | |
| | 25 | 4° C. | 105.02 | 100.79 | 101.19 | 96.24 | — | |
| | | 25° C./60% | 108.22 | 109.86 | 102.76 | 95.25 | — | |
| | | 40° C./75% | 108.05 | 109.77 | 100.54 | 92.29 | — | |
| F5 PVP K30 | 0 | 4° C. | 100.32 | 96.98 | 94.25 | 91.23 | — | |
| | | 25° C./60% | 100.14 | 89.05 | 71.16 | 55.20 | — | |
| | | 40° C./75% | 101.02 | 79.32 | 33.63 | 13.78 | — | |
| | 25 | 4° C. | 101.96 | 78.12 | 80.83 | 73.12 | — | |
| | | 25° C./60% | 100.93 | 94.88 | 68.14 | 39.11 | — | |
| | | 40° C./75% | 100.56 | 72.52 | 32.21 | 5.12 | — | |

All samples were within the specification of +10%/−5% of the target concentration of 100 mg/mL at the initial Day 0 assessment. Following 1 month of storage at each of the three storage conditions the three non-aqueous formulations (F1, F3 and F4) were still within the specification. However, the stability of F5 had already fallen out of specification at most storage conditions. At the 3 and 6 month assessment, formulations F2, F3 and F4 remained within the specification. However, based on the content of omeprazole in the gamma irradiated batch, formulation F3 showed superior stability at all storage conditions and was selected for further assessment. At 9 and 12 months after the commencement of the study F3 remained within the specification.

While the stability of formulations F1, F3 and F4 was shown to be very high, that of F3 was superior, even when stored at 40° C./75% RH for 9 months.

BIBLIOGRAPHY

Bell, N. J., D. Burget, C. W. Howden, J. Wilkinson and R. H. Hunt (1992). "Appropriate acid suppression for the management of gastro-oesophageal reflux disease." *Digestion* 51 Suppl 1: 59-67.

Merritt, A. M., L. C. Sanchez, J. A. Burrow, M. Church and S. Ludzia (2003). "Effect of GastroGard and three compounded oral omeprazole preparations on 24 h intragastric pH in gastrically cannulated mature horses." *Equine Veterinary Journal* 35(7): 691-695.

Sykes, B. W., M. Hewetson, R. J. Hepburn, N. Luthersson and Y. Tamzali (2015a). "European College of Equine Internal Medicine Consensus Statement—Equine Gastric Ulcer Syndrome in Adult Horses." *Journal of Veterinary Internal Medicine* 29(5): 1288-1299.

Sykes, B. W., C. M. McGowan and P. C. Mills (2015b). "Placement of an indwelling percutaneous gastrotomy (PEG) tube for the measurement of intra-gastric pH in two horses." *Equine Veterinary Education:* 27(12): 627-632.

Sykes, B. W., C. Underwood, C. M. McGowan and P. C. Mills (2015c). "Pharmacokinetics of intravenous, plain oral and enteric-coated oral omeprazole in the horse." *Journal of Veterinary Pharmacology and Therapeutics* 38(2): 130-136.

Shin, J. M. and G. Sachs (2008). "Pharmacology of Proton Pump Inhibitors." *Current gastroenterology reports* 10(6): 528-534.

Tellez, E., L. Ocampo, M. Bernad and H. Sumano (2005). "Pharmacodynamic study of a long-acting parenteral formulation of omeprazole in horses." *Journal of Veterinary Pharmacology and Therapeutics* 28(6): 587-589.

Sandin, A., F. M. Andrews, J. A. Nadeau, T. J. Doherty and G. Nilsson (1999). "Effects of intramuscular omeprazole on gastric acid secretion in horses over a twenty-four hour period." *Equine Veterinary Journal* 31(S29): 50-53.

The invention claimed is:

1. A method of treating and/or preventing gastric ulcers, said method comprising administering by injection a therapeutically effective amount of a non-aqueous liquid composition comprising:
(a) from 10 to 90% w/v of a first agent that is a medium chain triglyceride having three fatty acids, wherein at least two of the fatty acids each have an aliphatic tail of 6-12 carbon atoms, and the medium chain triglyceride has a viscosity at 20° C. of between 20 mPa·s and 70 mPa·s; and (b) from 50 mg/mL to 200 mg/mL of a second agent that is a proton pump inhibitor or pharmaceutically or veterinary acceptable salt, wherein the proton pump inhibitor is omeprazole, wherein:

the gastric ulcer is equine gastric ulcer syndrome;

the composition is adapted for sustained release of a therapeutically effective amount of the proton pump inhibitor to a subject in need thereof, wherein the method results in the sustained release of a therapeutically effective amount of the proton pump inhibitor over a period of at least 2 days, and wherein the composition is stable for at least 1 month.

2. The method of claim 1, wherein the concentration of the first agent is from 60-80% w/v.

3. The method of claim 1, wherein the proton pump inhibitor omeprazole, includes any pharmaceutically or veterinary analogs, enantiomers and polymorphs thereof and any pharmaceutically or veterinary equivalent salts thereof.

4. The method of claim 1, wherein the concentration of proton pump inhibitor in the composition is from 100 mg/ml to 150 mg/ml.

5. The method of claim 1, wherein the composition further comprises a stabilizer.

6. The method of claim 5, wherein the stabiliser is selected from the group consisting of:
a) an alkaline agent;
b) an amino acid; and
c) a basic amino acid.

7. The method of claim 5, wherein the stabiliser is L-arginine.

8. The method of claim 1, wherein the equine gastric ulcer syndrome is equine squamous gastric disease or equine glandular gastric disease.

9. The method of claim 1, wherein the composition is administered using a method selected from the group consisting of intramuscularly, subcutaneously, and intraperitoneally.

10. The method of claim 9, wherein the composition is administered intramuscularly.

11. The method of claim 1, wherein the method results in the sustained release of a therapeutically effective amount of the proton pump inhibitor over a period of time selected from the group consisting of 2 days, 3 days, 4 days, 5 days, 6 days, 1 week, 2 weeks, 3 weeks, 1 month, 2 months, 3 months, 4 months, 5 months, and 6 months.

12. The method of claim 1, wherein the method provides a minimum effective amount of the proton pump inhibitor in the subject's blood stream over a period of time selected from the group consisting of 2 days, 3 days, 4 days, 5 days, 6 days, 1 week, 2 weeks, 3 weeks, 1 month, 2 months, 3 months, 4 months, 5 months, and 6 months.

13. The method of claim 1, wherein the composition is administered using a dosing regimen selected from the group consisting of every two days, every three days, every four days, every five days, every six days, twice weekly, once weekly, every two weeks, every three weeks, once monthly, every two months, every three months, every four months, every five months, and every six months.

14. The method of claim 1, said method comprising administering by intramuscular injection a therapeutically effective amount of a non-aqueous liquid composition comprising:

a) from 10 to 90% w/v of a first agent that is a medium chain triglyceride having three fatty acids, wherein at least two of the fatty acids each have an aliphatic tail of 6-12 carbon atoms, and the medium chain triglyceride has a viscosity at 20° C. of between 20 mPa·s and 70 mPa·s; and b) from 50 mg/mL to 200 mg/mL of a second agent that is a proton pump inhibitor or pharmaceutically or veterinary acceptable salt, wherein the proton pump inhibitor is omeprazole; and c) a stabiliser comprising L-arginine wherein the gastric ulcer is equine gastric ulcer syndrome wherein the composition is adapted for sustained release of a therapeutically effective amount of the proton pump inhibitor to a subject in need thereof wherein the sustained release of the therapeutically effective amount of the proton pump inhibitor is over a period of time selected from the group consisting of 2 days, 3 days, 4 days, 5 days, 6 days, 1 week, 2 weeks, 3 weeks, 1 month, 2 months, 3 months, 4 months, 5 months, and 6 months and/or wherein the minimum effective amount of the proton pump inhibitor in the subject's blood stream is sustained over a period of time selected from the group consisting of 2 days, 3 days, 4 days, 5 days, 6 days, 1 week, 2 weeks, 3 weeks, 1 month, 2 months, 3 months, 4 months, 5 months, and 6 months.

15. The method of claim 1, wherein the composition is stable for at least a time period selected from the group consisting of 2 months, 3 months, 4 months, 5 months, 6 months, and 12 months.

16. The method of claim 15, wherein the composition is stable for at least 12 months.

17. The method of claim 1, wherein the method results in the sustained release of a therapeutically effective amount of the proton pump inhibitor over a period of at least 5 days.

18. The method of claim 1, wherein the at least two fatty acids of the medium chain triglyceride each have an aliphatic tail of 8-10 carbon atoms.

* * * * *